(12) United States Patent
Iwano et al.

(10) Patent No.: US 6,487,431 B1
(45) Date of Patent: Nov. 26, 2002

(54) RADIOGRAPHIC APPARATUS AND METHOD FOR MONITORING THE PATH OF A THRUST NEEDLE

(75) Inventors: Teruaki Iwano, Tokushima; Yoshinori Yamashita, Kyoto; Takashi Marume, Otsu, all of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/396,436

(22) Filed: Sep. 15, 1999

(30) Foreign Application Priority Data

Oct. 27, 1998 (JP) .......................... 10-305396
Jun. 28, 1999 (JP) .......................... 11-181701

(51) Int. Cl.⁷ .............................. A61B 5/05; A61B 6/00
(52) U.S. Cl. ..................... 600/407; 600/427; 600/411; 606/130
(58) Field of Search ................. 600/429, 417, 600/424, 407, 411, 427; 378/20, 206; 606/130; 604/21

(56) References Cited

U.S. PATENT DOCUMENTS

| | | | | |
|---|---|---|---|---|
| 5,868,675 A | * | 2/1999 | Henrion et al. | 600/424 |
| 6,006,127 A | * | 12/1999 | Van Der Brug et al. | 600/427 |
| 6,041,249 A | * | 3/2000 | Regn | 600/429 |
| 6,064,904 A | * | 5/2000 | Yanof et al. | 600/414 |
| 6,216,029 B1 | * | 4/2001 | Paltieli | 600/427 |

* cited by examiner

*Primary Examiner*—Shawna J. Shaw
(74) *Attorney, Agent, or Firm*—Rader, Fishman & Grauer, PLLC (57) ABSTRACT

A radiographic apparatus is disclosed, which allows a biopsy needle or a drug injection needle to be run into a patient accurately and quickly. Once a needle entry point on a body surface of the patient and a target point in the patient are designated and inputted on the screen of a display monitor, the radiographic apparatus in this invention automatically displays, en block on the display monitor, a guideline linking the two points, intersection marks indicative of intersections of the guideline and CT images, and angles and length serving as a reference for determining a direction and depth of running the needle. The operator has only to run the needle to a required depth along the guideline and intersection marks in the direction indicated by the angles displayed. Thus, the biopsy needle or injection needle may be run into the patient accurately and quickly.

11 Claims, 12 Drawing Sheets

RADIOGRAPHIC APPARATUS AND METHOD FOR MONITORING THE PATH OF A THRUST NEEDLE

BACKGROUND OF THE INVENTION (1) Field of the Invention

This invention relates to a radiographic apparatuses such as an X-ray CT apparatus or MRI apparatus for use in thrusting a biopsy needle into a patient to remove a tissue from the patient for biopsy, or an injection needle into a patient to inject an anti-cancer drug or compound into a diseased part of the patient. More particularly, the invention relates to a technique of predicting a running path of a biopsy needle or injection needle (which may be called collectively hereinafter "thrust needle").

(2) Description of the Related Art

In examining and treating cancer at medical institutions, a thrust needle is run into the patient's body to remove a tissue for biopsy or inject an anti-cancer drug or compound into a diseased part. In one conventional method, for example, a thrust needle is run into the patient while monitoring running conditions of the needle by means of fluoroscopy provided by an X-ray CT apparatus. This practice will be described hereinafter, taking a biopsy needle for example.

Figure 1:
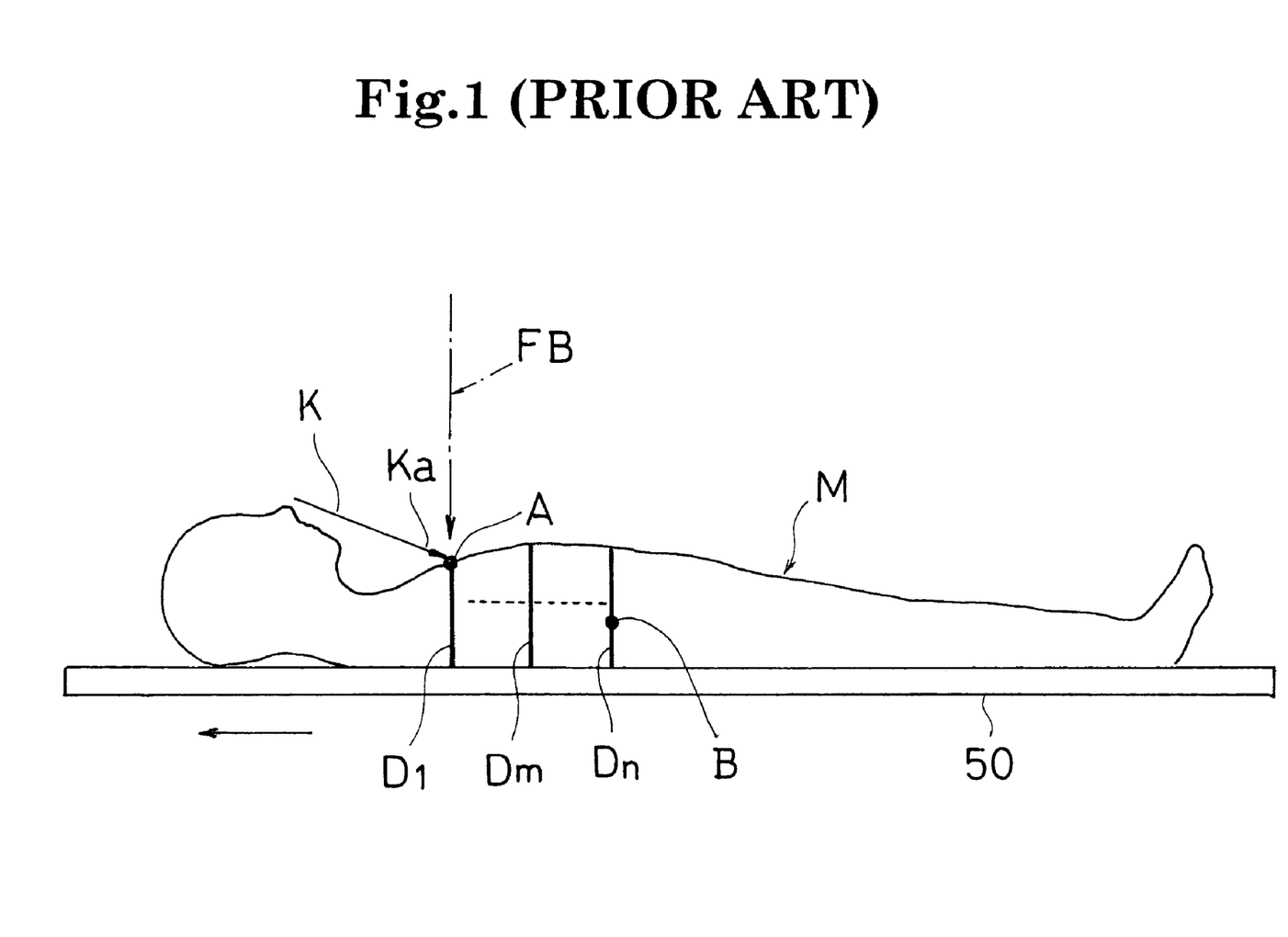
FIG. 1 is a schematic perspective view showing an outline of a radiographic process by a conventional apparatus.
Figure 2A:
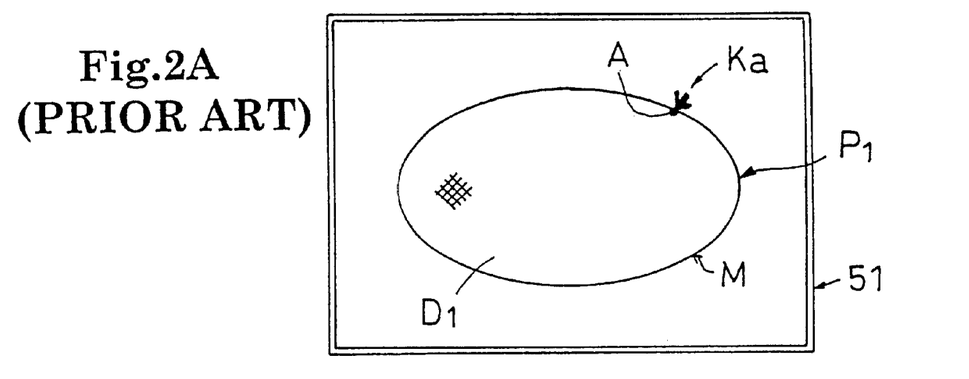
FIGS. 2A through 2C are front views of a display screen of the conventional apparatus showing different running stages of a biopsy needle.

In this method, as shown in FIG. 1, a fan beam FB is emitted from an X-ray tube (not shown) to a cross section (slice plane) D1 including a needle entry point A of a patient M lying on a top board 50. An X-ray detector (not shown) outputs X-ray detection data for providing a sectional image P1 of slice plane D1 which is displayed in real time on the screen of a display monitor 51 as shown in FIG. 2A, Then, a biopsy needle K is put to the needle entry point on the body of patient M. The operator, while looking at the screen of display monitor 51 to rely on what is seen thereon, gradually advances the biopsy needle K toward a tissue collection point B. At the same time, the top board 50 is moved for a fan beam FB to irradiate successively from the slice plane D1 including the needle entry point A to a slice plane Dn including the tissue collection point (goal) B.

Figure 2B:
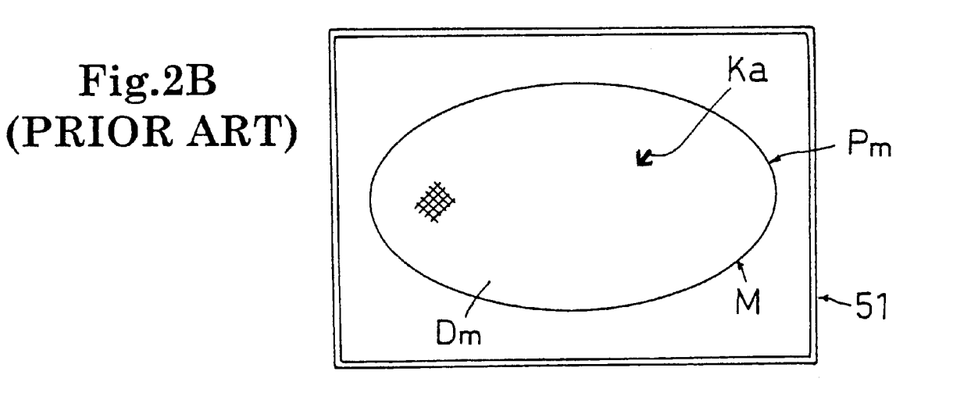

As a result, different sectional images are successively displayed on the screen of display monitor 51. As shown in FIG. 2B, the point Ka of biopsy needle K appears with a sectional image Pm on the screen of display monitor 51. This enables the operator to continue advancing the biopsy needle K while constantly monitoring running conditions of the biopsy needle K on the screen of display monitor 51.

Figure 2C:
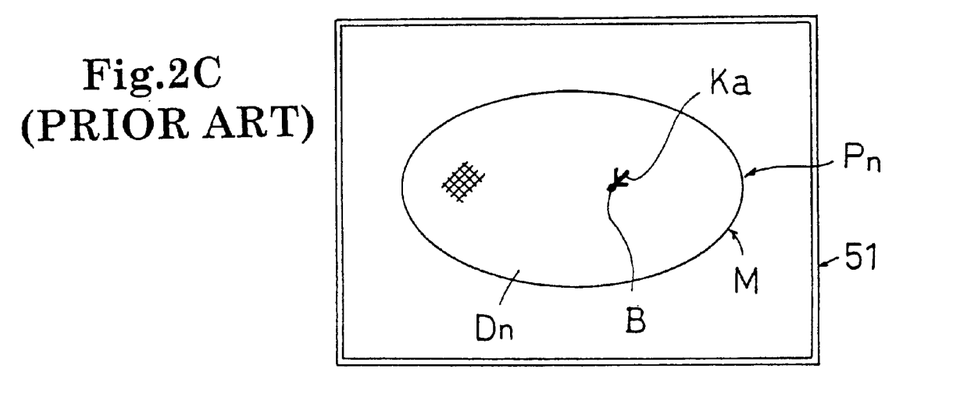

Finally, as shown in FIG. 2C, the point Ka of biopsy needle K reaches the tissue collection point B in a sectional image Pn of slice plane Dn of the patient M. Upon confirmation of this position of biopsy needle K, the needle running operation per se is completed.

However, where a conventional X-ray CT apparatus or the like is used in running a biopsy needle into a patient, it is difficult to secure an accurate running path of the biopsy needle. Moreover, the conventional practice of running the biopsy needle has a drawback of taking a very long time.

In running the biopsy needle K, the operator predicts a running path of biopsy needle K by observing only sectional images of slice planes of the patient M. It is difficult to predict a running path of biopsy needle K accurately by relying only on the sectional images of slice planes of the patient M. An inaccurate prediction of a running path of biopsy needle K will fail to secure an accurate running path of biopsy needle K.

In addition, between the needle entry point A and tissue collection point B, there may be vulnerable organs which must not be penetrated by the needle, or hard bones impenetrable by the needle. The operator has to run the biopsy needle K clear of such vulnerable organs and hard bones in a manner of trial and error relying on visual observation. This needle running operation consumes a long time.

SUMMARY OF THE INVENTION

This invention has been made having regard to the state of the art noted above, and its object is to provide a radiographic apparatus for enabling a thrust needle to be run through an accurate running path in an expeditious way.

The above object is fulfilled, according to this invention, by a radiographic apparatus for shifting slice planes imaged of a patient and displaying sectional images of the slice planes in real time on a display monitor in response to running of a thrust needle into the patient, in order to assist in running the thrust needle from a body surface of the patient to a target point in the patient, the apparatus comprising a screen input device for designating and inputting a needle entry point on the body surface of the patient and the target point in the patient, on a screen of a display monitor displaying the sectional images, and a guideline computing and displaying unit for computing a line segment linking the needle entry point and the target point, and displaying the line segment as a guideline superposed on the sectional images for guiding the thrust needle.

According to this invention, when running a thrust needle into a patient, sectional images including a needle input point on a body surface of the patient and a target point in the patient are displayed on the display monitor, and the screen input device is operated to designate and input the needle input point and target point on the screen. Then, the guideline computing and displaying unit immediately computes a line segment linking the needle input point and target point. The line segment computed is automatically displayed as a guideline superposed on the sectional images. Based on the guideline displayed as superposed on the sectional images on the screen of the display monitor, the operator may immediately determine whether a needle running path is appropriate or not. When the running path is found appropriate, the operator has only to run the thrust needle along the guideline. That is, with the apparatus according to this invention, the guideline serves as a reference for running the thrust needle, whereby a needle running operation may be carried out accurately and quickly. When the running path is found inappropriate, a needle entry point or a target point is designated all over again to compute and display a new guideline.

Preferably, the radiographic apparatus according to this invention further comprises an intersection computing and displaying unit for successively computing intersections of the slice planes and the guideline in response to shifting of the slice planes, and displaying intersection marks indicative of the intersections as superposed on the sectional images. When the thrust needle correctly runs along the guideline, the needle point never fails to meet the intersections computed. Thus, the operator has only to run the thrust needle in a way that the needle point coincides with the intersection marks representing the intersections computed. That is, the intersection marks representing the intersections serve as a reference for guiding the needle point to an exact position, whereby a needle running operation may be carried out accurately and quickly.

Preferably, the radiographic apparatus according to this invention further comprises a slice width range computing and displaying unit for successively computing slice width ranges each extending between opposite ends of a portion of the guideline present within a slice thickness across each of the slice planes in response to shifting of the slice planes, and displaying the slice width ranges of the guideline as superposed on the sectional images. With this construction, the operator runs the thrust needle to move the needle point precisely from the starting end to the finishing end of each slice width range of the guideline. That is, each sectional image on which the guideline is superposed includes data within its slice thickness combined and, so to speak, compressed thereinto. The thrust needle, strictly speaking, is run along the guideline just by an amount equal to the slice thickness. Thus, when the operator correctly runs the thrust needle based on each sectional image, the needle point moves precisely from the starting end to the finishing end of each slice width range of the guideline. Thus, the slice width range of the guideline superposed on each sectional image serves as a reference for guiding the needle point throughout the slice thickness to an exact position.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

First Embodiment

Figure 3:
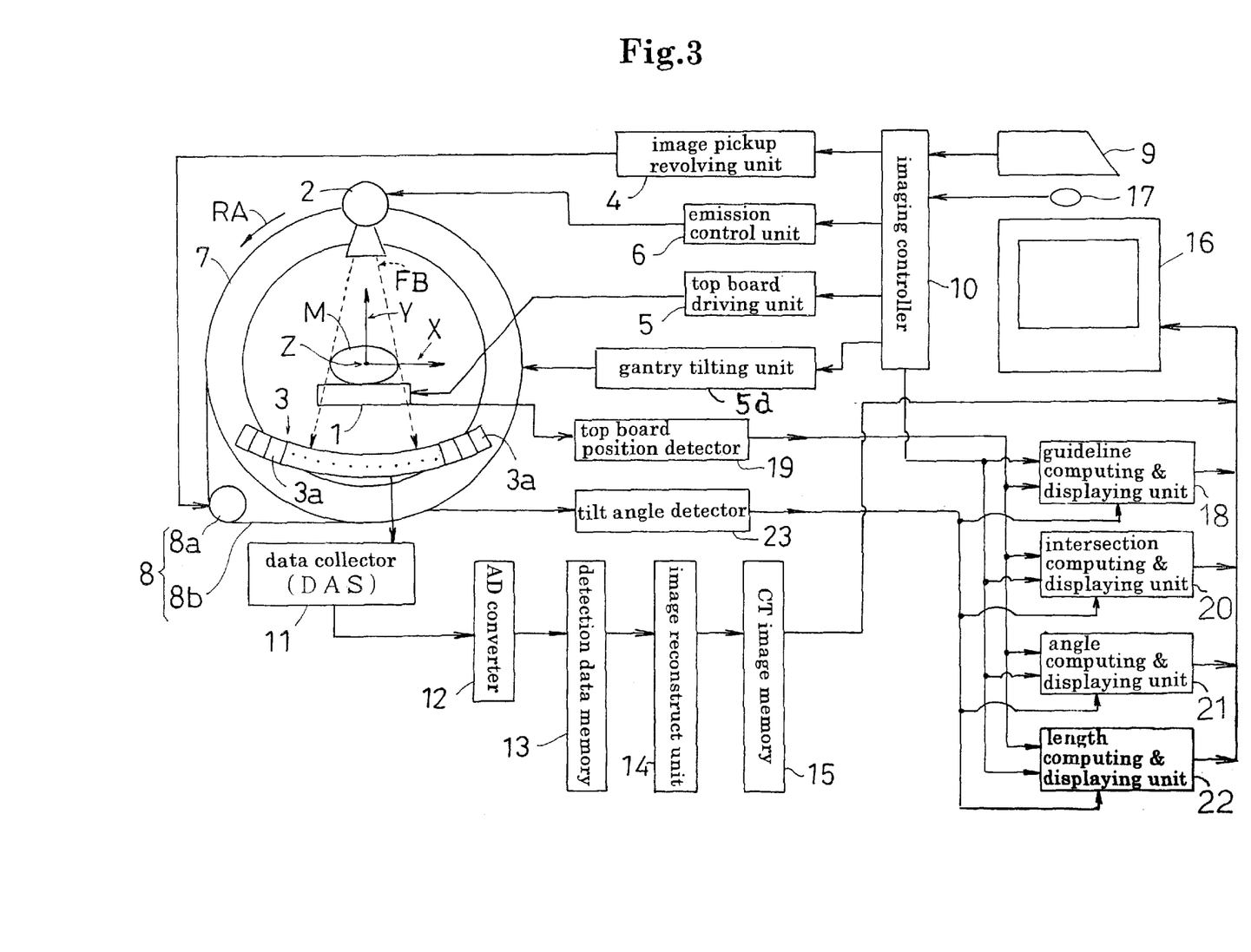
FIG. 3 is a block diagram of an entire X-ray CT apparatus in a first embodiment of this invention.

FIG. 3 is a block diagram of an entire X-ray CT apparatus in a first embodiment of this invention. In the following description, this apparatus will be used in thrusting a biopsy needle into a patient. It should be understood, however, that this invention is applicable also to a case of thrusting an injection needle into a patient to inject an anti-cancer drug or compound into a diseased part of the patient.

As shown in FIG. 3, the X-ray CT apparatus in this embodiment includes a movable top board 1, and an image pickup having an X-ray tube 2 for emitting X rays and an X-ray detector 3 for detecting transmitted X rays. The X-ray tube 2 and X-ray detector 3 are opposed to each other across a patient M lying on the top board 1. The apparatus further includes an image pickup revolving unit 4 for revolving the X-ray tube 2 and X-ray detector 3, as opposed to each other, about the body axis of patient M in a direction indicated by an arrow RA.

The top board 1 is constructed movable fore and aft with the patient M placed thereon. The top board 1 is moved under control of a top board driving unit 5.

The X-ray tube 2, while in revolution, irradiates the patient M with a fan beam FB with selected irradiating conditions such as a tube voltage and a tube current, under control of an emission control unit 6 including a high voltage generator.

The X-ray detector 3 is a multi-channel detector having numerous, e.g. in the order of 1000, X-ray detecting elements 3a arranged along an expanse of fan beam FB. The X-ray detector 3 revolving with the X-ray tube 2 outputs X-ray detection data as the fan beam FB is emitted from the X-ray tube 2.

The image pickup in this embodiment further includes a rotary ring 7 fixedly supporting the X-ray tube 2 and X-ray detector 3, and a ring rotating mechanism 8 having a pulley 8a and a belt 8b. Under control of the image pickup revolving unit 4, the ring rotating mechanism 8 rotates the rotary ring 7 to revolve the X-ray tube 2 and X-ray detector 3 in unison.

The image pickup revolving unit 4, top board driving unit 5 and emission control unit 6 perform the respective controls upon instructions from an imaging controller 10. These instructions are outputted at appropriate times in response to inputs made through a console 9 or the like.

In this embodiment, the X-ray detection data outputted from the X-ray detector 3 as the fan beam FB is emitted from the X-ray tube 2 is collected in a data collector (DAS) 11, and is thereafter transmitted to an analog-to-digital converter 12 for digitizing the data. Following the analog-to-digital converter 12 in arrangement are a detection data memory 13 for storing the X-ray detection data, an image reconstruct unit 14 for performing a three-dimensional image reconstructing process based on the X-ray detection data, a CT image memory 15 for temporarily storing (X-ray) CT images made, and a display monitor 16 for displaying the CT images.

Figure 4:
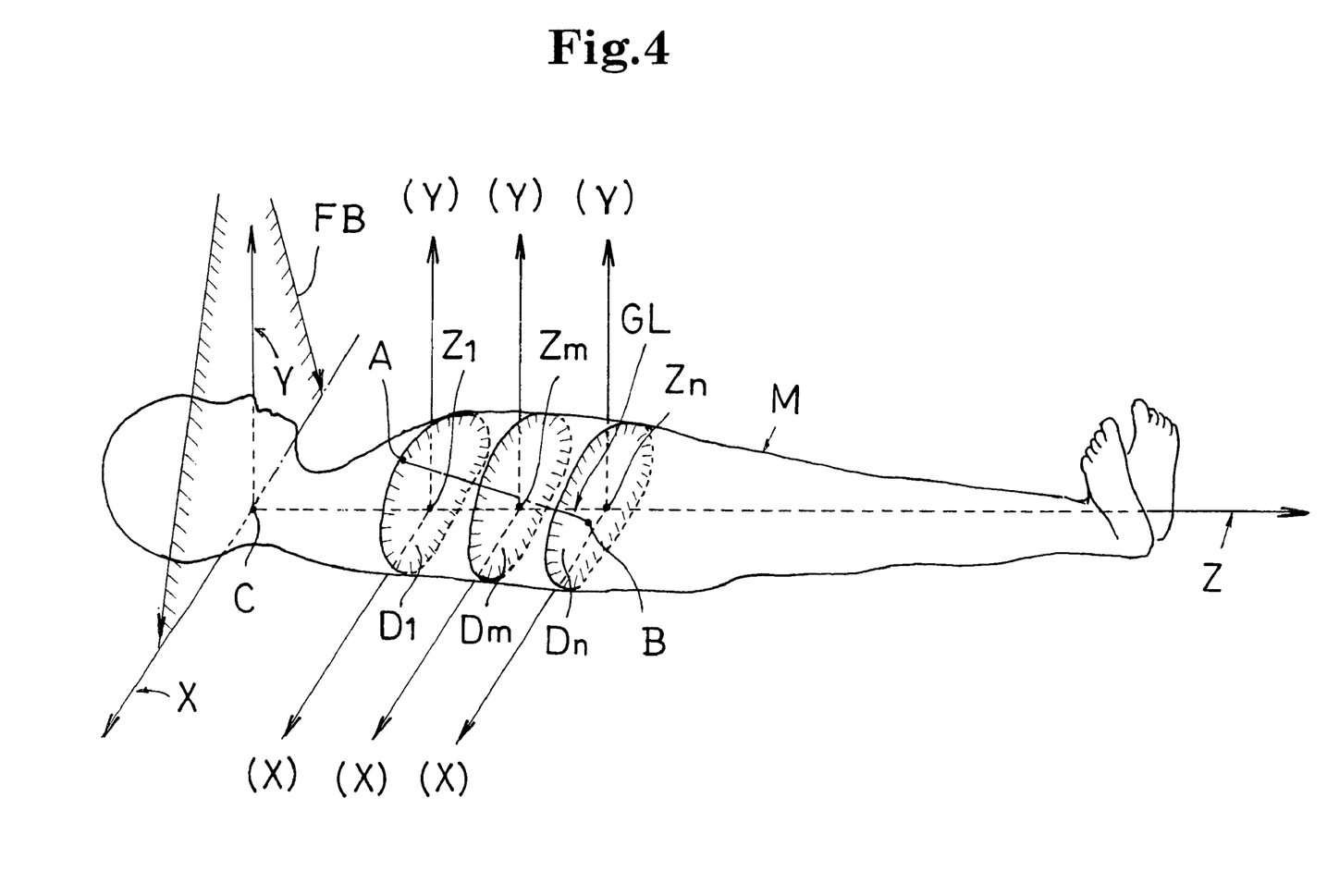
FIG. 4 is a schematic perspective view showing an outline of a radiographic process in the first embodiment.
Figure 5:
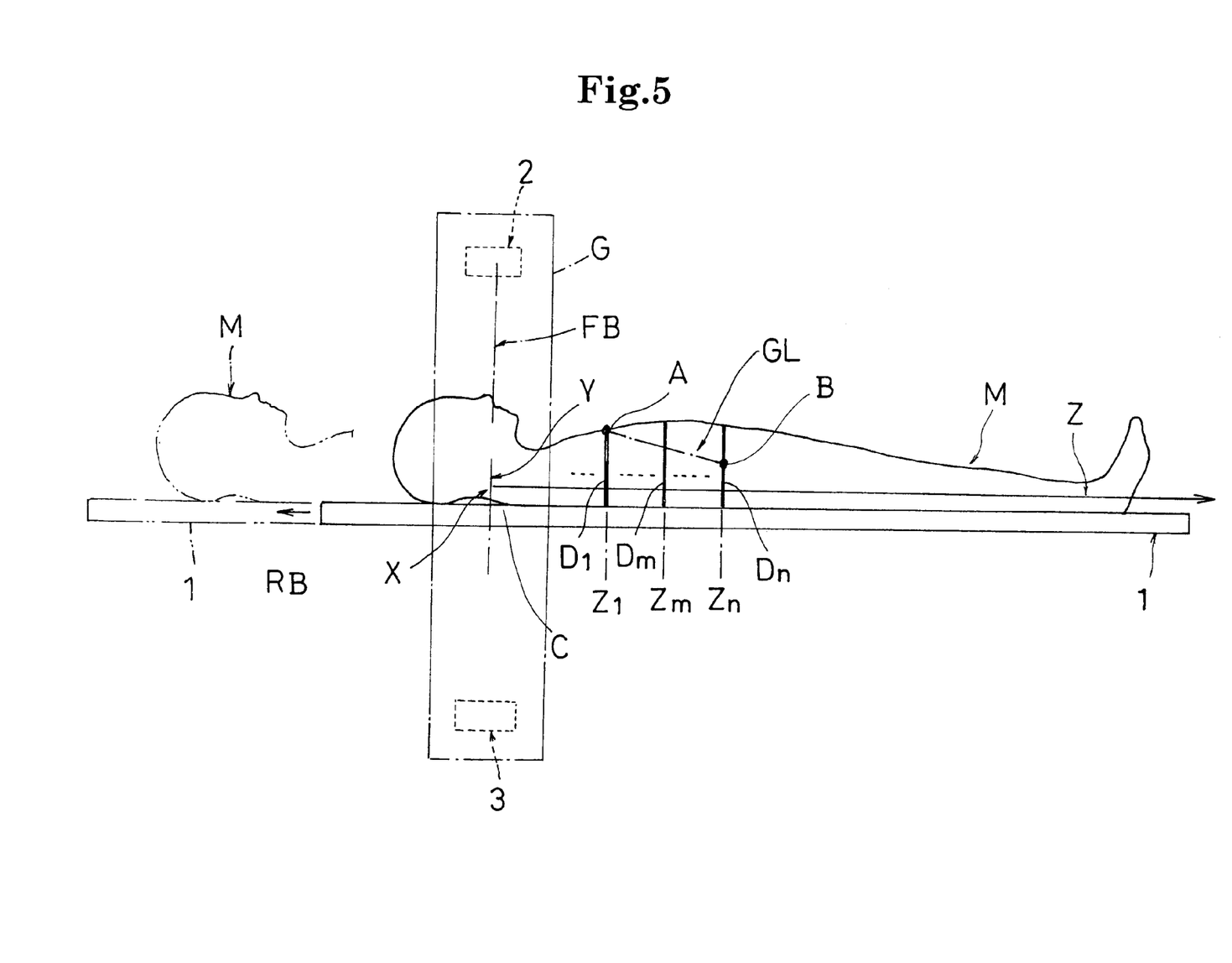
FIG. 5 is a schematic front view showing an outline of the radiographic process in the first embodiment.

As shown in FIGS. 4 and 5, the image pickup in this embodiment has, set as device coordinates, XYZ rectangular coordinates with origin C coinciding with the center of imaging in the gantry G. In performing radiography, the patient M is placed on the top board 1, with his or her body axis aligned to Z-axis. Subsequently, as shown in FIG. 4, the fan beam FB is emitted to travel through an XY plane including the origin C. This provides a CT image of a slice plane of patient M coinciding with the XY plane. Actually, CT images may be picked up by tiling the gantry G at a predetermined angle. To facilitate understanding, it is assumed here that CT images are picked up as coinciding with the XY plane.

Thus, as shown in FIG. 5, the top board 1 is moved along Z-axis as indicated by an arrow RB, to bring Z-coordinates, $Z_1, \ldots Z_n$, indicative of current positions of patient M to the origin C, for example. In this way, CT images of selected slice planes $D_1, \ldots D_n$ (perpendicular to the body axis) of patient M may be acquired one after another. It will be appreciated that the center of screen coordinates on display monitor 16 for displaying the CT images is set in a corresponding relationship to the origin C of the device coordinates.

The X-ray CT apparatus in this embodiment has various features useful in thrusting a biopsy needle into the patient M to remove a tissue therefrom for biopsic examination.

This apparatus includes a mouse (screen input device) 17 for designating a needle entry point A and a tissue collection point (goal) B on/in the patient M on the screen of display monitor 16 displaying CT images. The apparatus includes also a guideline computing and displaying unit 18 for computing a line segment between the needle entry point A and tissue collection point B designated with the mouse 17, and displaying the segment as a guideline GL superposed on the CT images for running the biopsy needle.

It is assumed here that, as shown in FIGS. 4 and 5, the needle entry point A is located at an outer edge of slice plane D1 at current Z coordinate Z1, while the tissue collection point B is located at or adjacent the center of slice plane Dn of current Z coordinate Zn.

Figure 6:
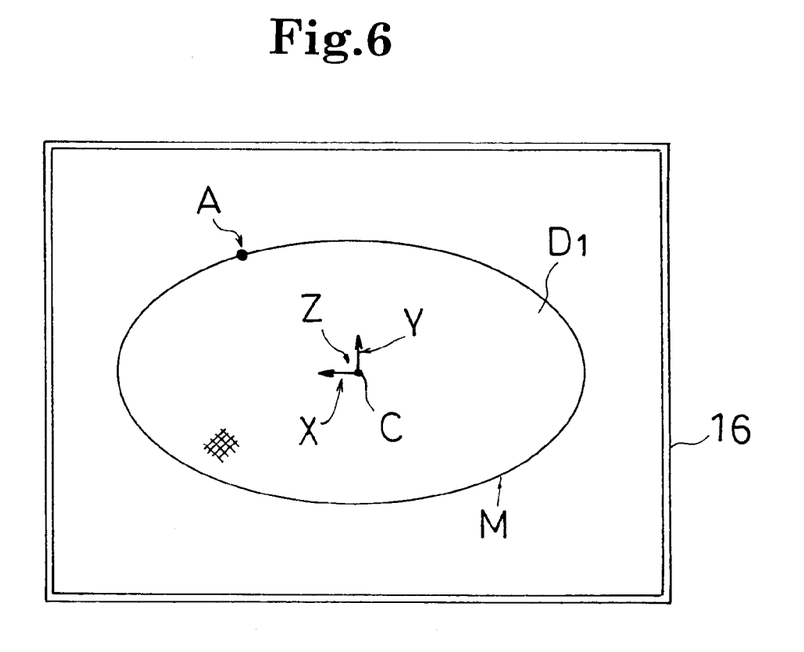
FIG. 6 is a front view of an input screen showing a needle entry point in the first embodiment.

For inputting the needle entry point A on the screen, as shown in FIG. 6, the CT image of slice plane D1 is displayed on the screen of display monitor 16, and the mouse 17 is clicked after moving the cursor to the position of needle entry point, A. Then, the imaging controller 10 reads XY coordinates (X1, Y1) (corresponding to the device coordinate system) of the needle entry point A from the input point on the screen of display monitor 16, and reads Z coordinate (Z1) (corresponding to the device coordinate system) of needle entry point A from an amount of movement of top board 1 from the origin C which is transmitted from a top board position detector 19. The three coordinates read of needle entry point A are transmitted to the guideline computing and displaying unit 18.

Figure 7:
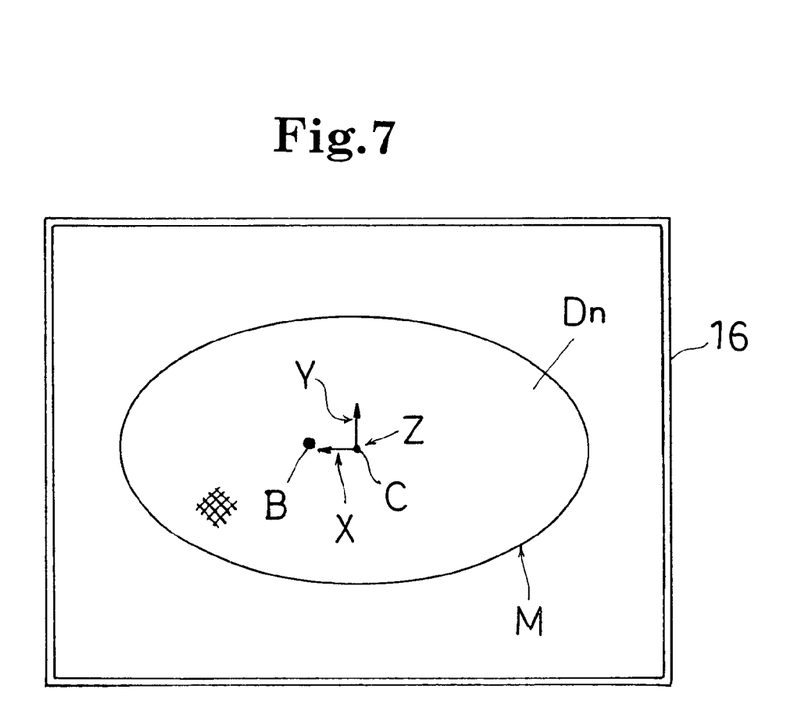
FIG. 7 is a front view of an input screen showing a tissue collection point in the first embodiment.

For inputting the tissue collection point B on the screen, as shown in FIG. 7, the CT image of slice plane Dn is displayed on the screen of display monitor 16, and the mouse 17 is clicked after moving the cursor to the position of tissue collection point B. Then, the imaging controller 10 reads XY coordinates (Xn, Yn) (corresponding to the device coordinate system) of the tissue collection point B from the input point on the screen of display monitor 16, and reads Z coordinate (Zn) (corresponding to the device coordinate system) of tissue collection point B from an amount of movement of top board 1 from the origin C which is transmitted from the top board position detector 19. The three coordinates read of tissue collection point B are transmitted to the guideline computing and displaying unit 18.

Figure 8:
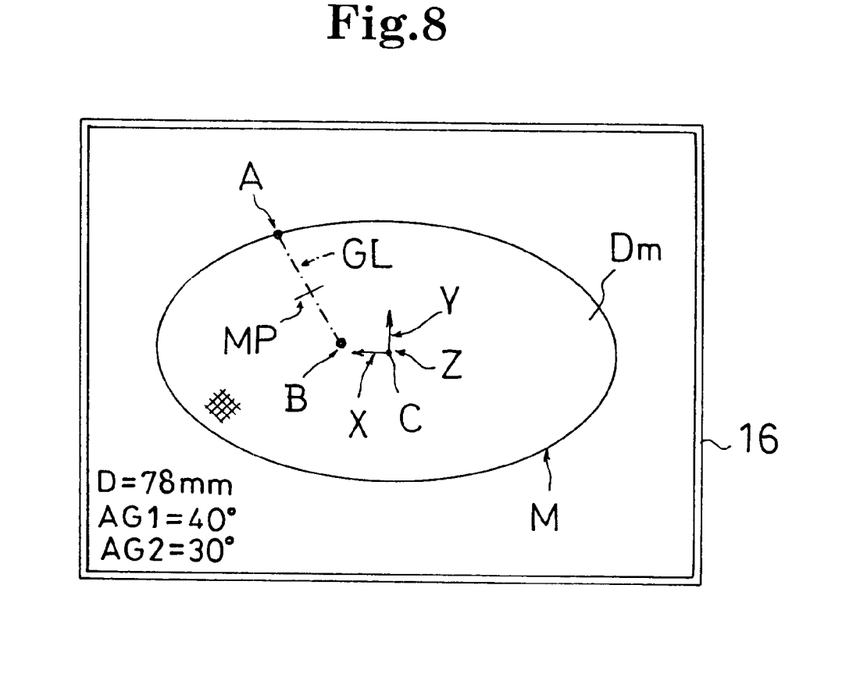
FIG. 8 is a front view of a display screen showing a guideline in the first embodiment.

The guideline computing and displaying unit 18 immediately computes guideline GL from the coordinates of the two points A and B. As shown in FIG. 8, the guideline GL is displayed as superposed on the CT images on the screen of display monitor 16. FIG. 8 shows a CT image of slice plane Dm. The operator uses the guideline GL as a reference for selecting a running path of the biopsy needle. Although the guideline GL extending between the two points A and B usually is a straight line in the three-dimensional coordinate system, each CT image on the display monitor 16 shows a two-dimensional guideline GL projected on its slice plane.

The apparatus in this embodiment further includes an intersection computing and displaying unit 20 for successively computing intersections of the slice planes imaged and the three-dimensional guideline GL in response to movement of the top board 1, and displaying an intersection mark MP indicative of each intersection computed, in superposition on the CT image as shown in FIG. 8.

Where the points A and B are located in different slice planes, each slice plane imaged and the guideline GL intersect only at one point, and different slice planes imaged have different points of intersection with the guideline GL. It is therefore necessary to compute one position of intersection after another following movement of the top board 1 (following changes of slice planes at the origin C).

Figure 9:
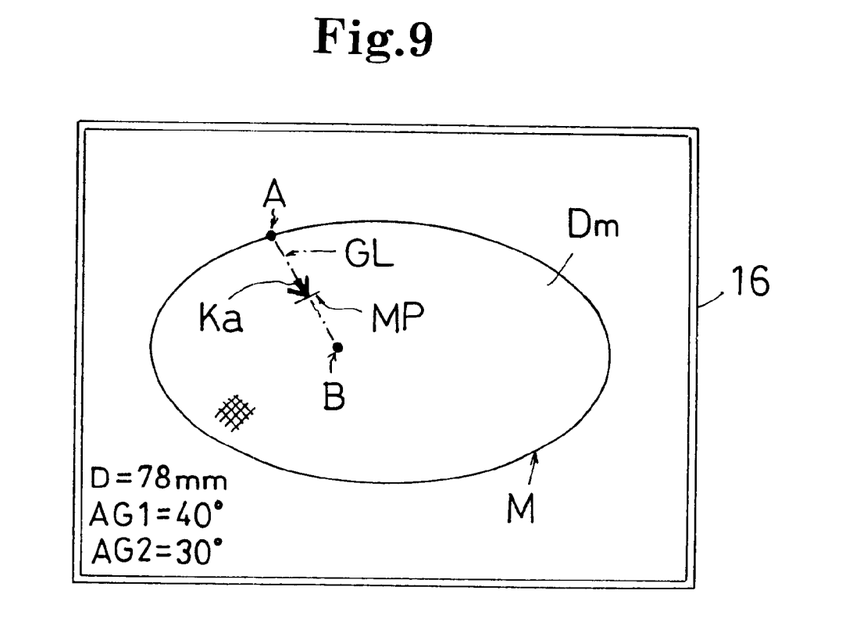
FIG. 9 is a front view of a display screen showing a running stage of a biopsy needle in the first embodiment.

When thrusting in the biopsy needle K, as shown in FIG. 9, the needle point Ka is set to the intersection mark MP. Since the fan beam FB has a certain thickness, part of the biopsy needle K appears in the CT image.

Further, the apparatus in this embodiment includes an angle computing and displaying unit 21 for computing an angle AG1 formed between guideline GL and Z-axis (reference axis) and an angle AG2 between guideline GL and Y-axis (reference axis), and simultaneously displaying numerical values representing the angles AG1 and AG2 on the display monitor 16 as shown in FIG. 8. The apparatus includes also a length computing and displaying unit 22 for computing a length D of guideline GL, and simultaneously displaying a numerical value representing the length D on the display monitor 16 as shown in FIG. 8.

The operator can presume a direction in which the biopsy needle K should be thrusted, from the numerical values of angles AG1 and AG2 computed. For example, the operator sets the biopsy needle K in vertical posture to the needle entry point A, and then tilts the needle K at the angle AG1 to Z-axis and at the angle AG2 to Y-axis. As a result, the biopsy needle K is aligned to the guideline GL.

Further, the operator can presume a depth to which the biopsy needle K should be thrusted, from the numerical value of length D computed. The biopsy needle K usually is graduated from the point toward the other end. The operator thrusts in the biopsy needle K as far as a graduation mark corresponding to the numerical value of length D computed.

Figure 10:
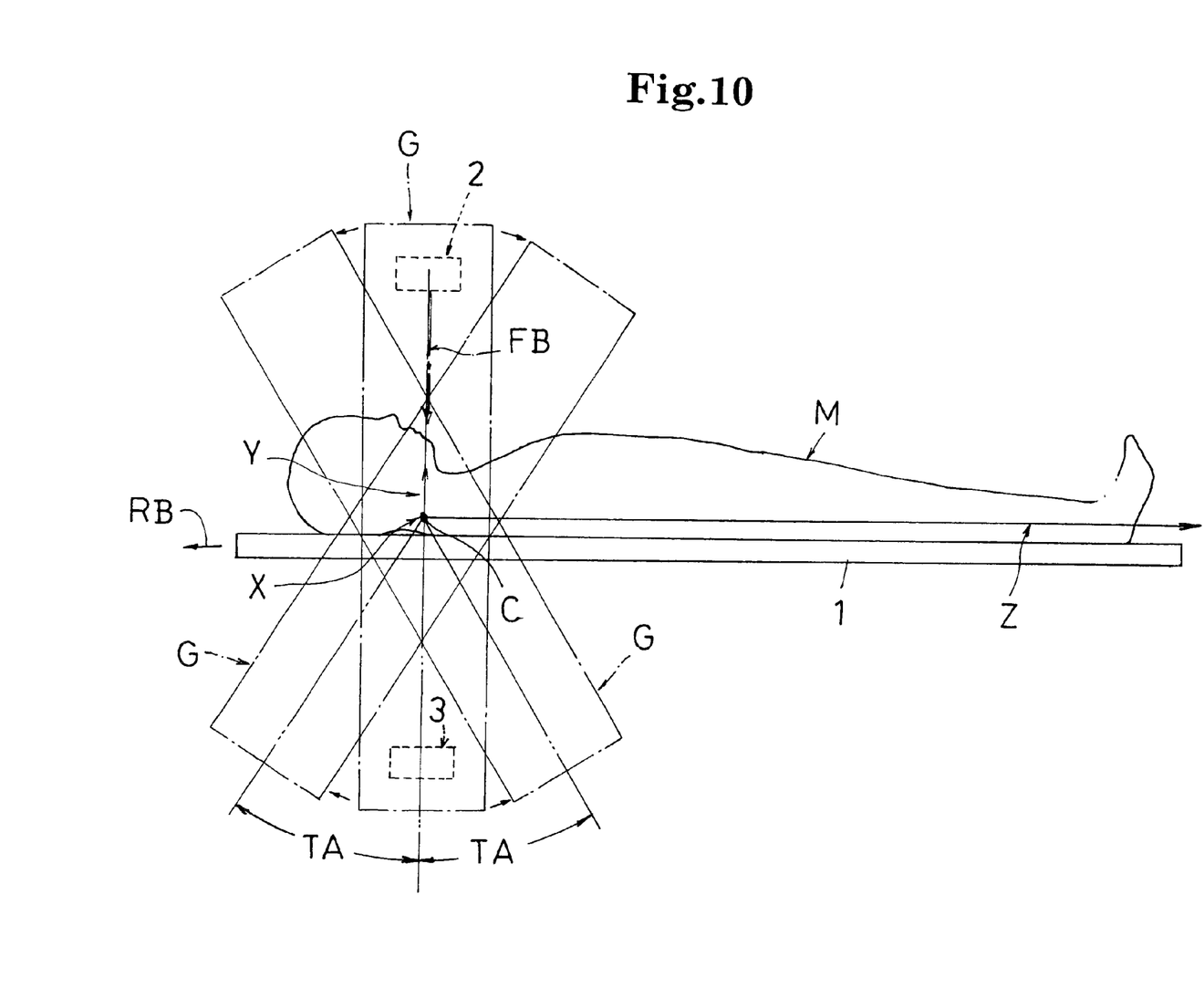
FIG. 10 is a front view showing tilting of a gantry in the first embodiment.

The X-ray CT apparatus in this embodiment not always picks up images from slice planes perpendicular to the body axis of patient M as described above, but may pick up images from slice planes inclined with respect to the body axis of patient M with the gantry C tilted at an angle TA by a gantry tilting unit 5a as shown in FIG. 10. In this case, the tilt angle TA of gantry G must be taken into account when computing the guideline GL, intersections of guideline GL and CT images, angles AG1 and AG2 indicating a direction of guideline GL, and length D of guideline GL. The apparatus in this embodiment includes a tilt angle detector 23 for detecting the tilt angle TA of gantry G, and transmitting the tilt angle TA to the computing and displaying units 18 and 20–22. Based on the tilt angle TA, these units 18 and 20–22 replace the respective coordinates with the device coordinates.

In this embodiment, the image reconstruct unit 14 and computing and displaying units 18 and 20–22 are formed chiefly of a computer and operative programs (software).

Figure 11:
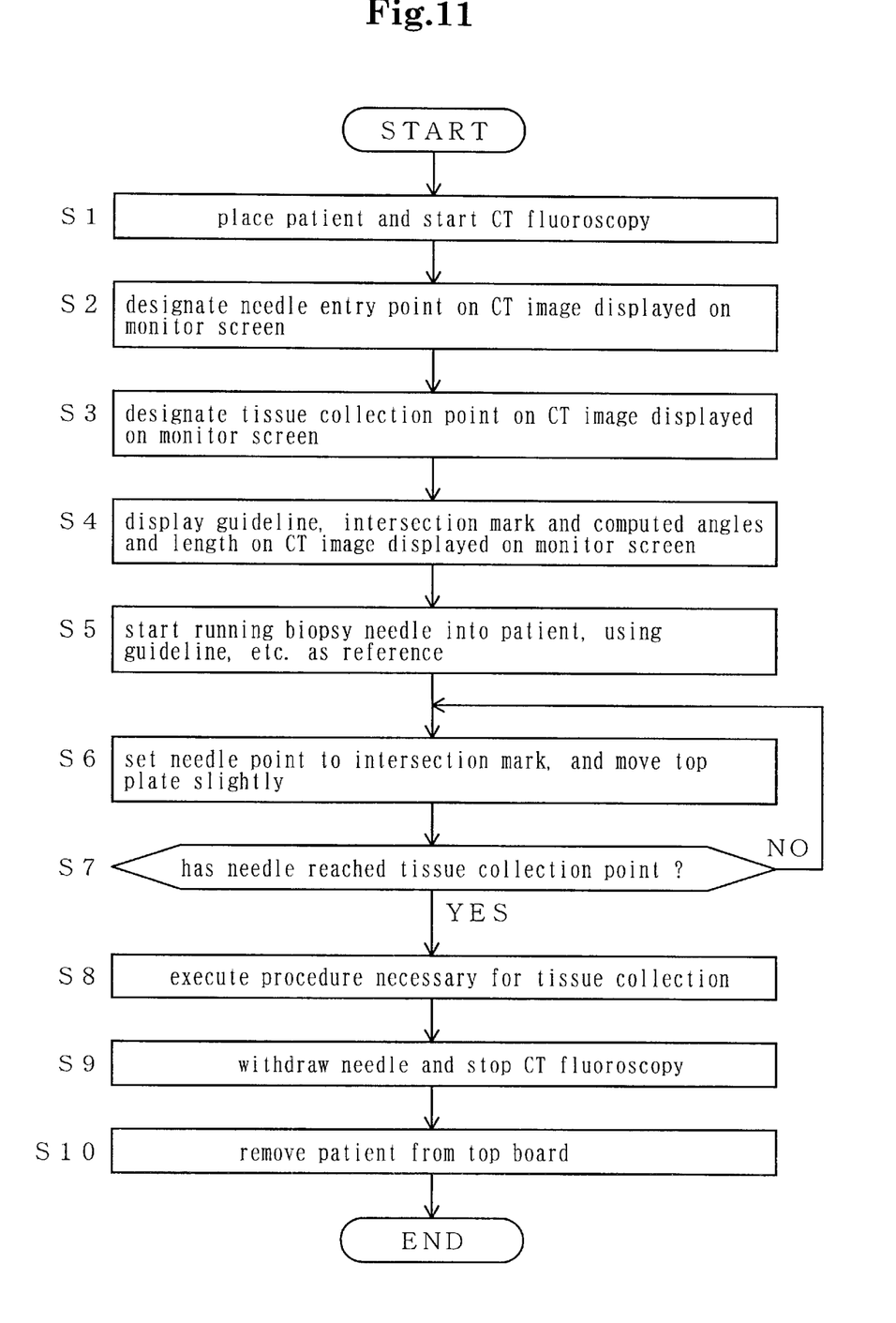
FIG. 11 is a flow chart of a sequence of tissue collection with the biopsy needle in the first embodiment.

Next, an operation of the apparatus having the above construction will be described with reference to the drawings. In this operation, the biopsy needle is run into the patient M to remove tissue with an aid of CT fluoroscopy. FIG. 11 is a flow chart of a sequence of tissue collection with the biopsy needle.

[Step S1] The patient M from whom tissue is to be removed for biopsy is placed on the top board 1. While moving the top board 1 along Z-axis, the patient M is irradiated with fan beam FB. A CT fluoroscopy is started to display CT images of slice planes of patient M on the display monitor 16 at a fast rate of 8 images per second, for example.

[Step S2] When the CT image of slice plane D1 with the needle entry point A is displayed on the screen of display monitor 16 as shown in FIG. 6, the movement of top board 1 is temporarily stopped. The mouse 17 is clicked on the needle entry point A, and the top board 1 is moved again.

[Step S3] When the CT image of slice plane Dn with the tissue collection point B is displayed on the screen of display monitor 16 as shown in FIG. 7, the movement of top board 1 is temporarily stopped. The mouse 17 is clicked on the tissue collection point B.

[Step S4] Upon designation of the two points A and B, the guideline GL, intersection mark MP, and computed angles AG1 and AG2 and length D of guideline GL are displayed on the screen of display monitor 16.

[Step S5] The top board 1 is returned to the position where the CT image of slice plane D1 is displayed on the screen of display monitor 16. The operator starts thrusting the biopsy needle K, using the computed angles AG1 and AG2 as a reference.

[Step S6] After the point Ka of biopsy needle K is set to the intersection mark MP on the screen of display monitor 16 as shown in FIG. 9, the top board 1 is moved slightly.

[Step S7] Step 6 is repeated, using the numerical value of length D of guideline GL as a reference, until the point Ka of biopsy needle K reaches the tissue collection point B. When the point Ka of biopsy needle K has reached the tissue collection point B, the operation proceeds to step S8.

[Step S8] A procedure necessary for removing a tissue for biopsic examination is executed.

[Step S9] Upon completion of the procedure necessary for removing a tissue, the biopsy needle K is withdrawn quickly and the CT fluoroscopy is stopped when appropriate.

[Step S10] The patient M is removed from the top board 1 to complete the tissue collection for biopsy.

With the X-ray CT apparatus in this embodiment described above, the guideline GL linking the needle entry point A and tissue collection point B is displayed as superposed on the CT images on the screen of display monitor 16. The operator can accurately predict a running path of biopsy needle K, so that the running path of biopsy needle K be exact at all times. In addition, the guideline GL serves as a reference in time of running the biopsy needle K, whereby the biopsy needle K may be run quickly.

The apparatus in this embodiment displays the intersection marks MP as superposed on the CT images to act as a reference for guiding the needle point Ka to a correct position. Thus, the operator may run the biopsy needle K into the patient M accurately and quickly.

Further, the apparatus in this embodiment displays also the computed angles AG1 and AG2 and length D of guideline GL on the display monitor 16. The angles AG1 and AG2 act as a reference for determining a direction of running the biopsy needle K, while the length D acts as a reference for determining a depth of running the biopsy needle K. Thus, the operator may run the biopsy needle K into the patient M accurately and quickly.

Second Embodiment

Figure 12:
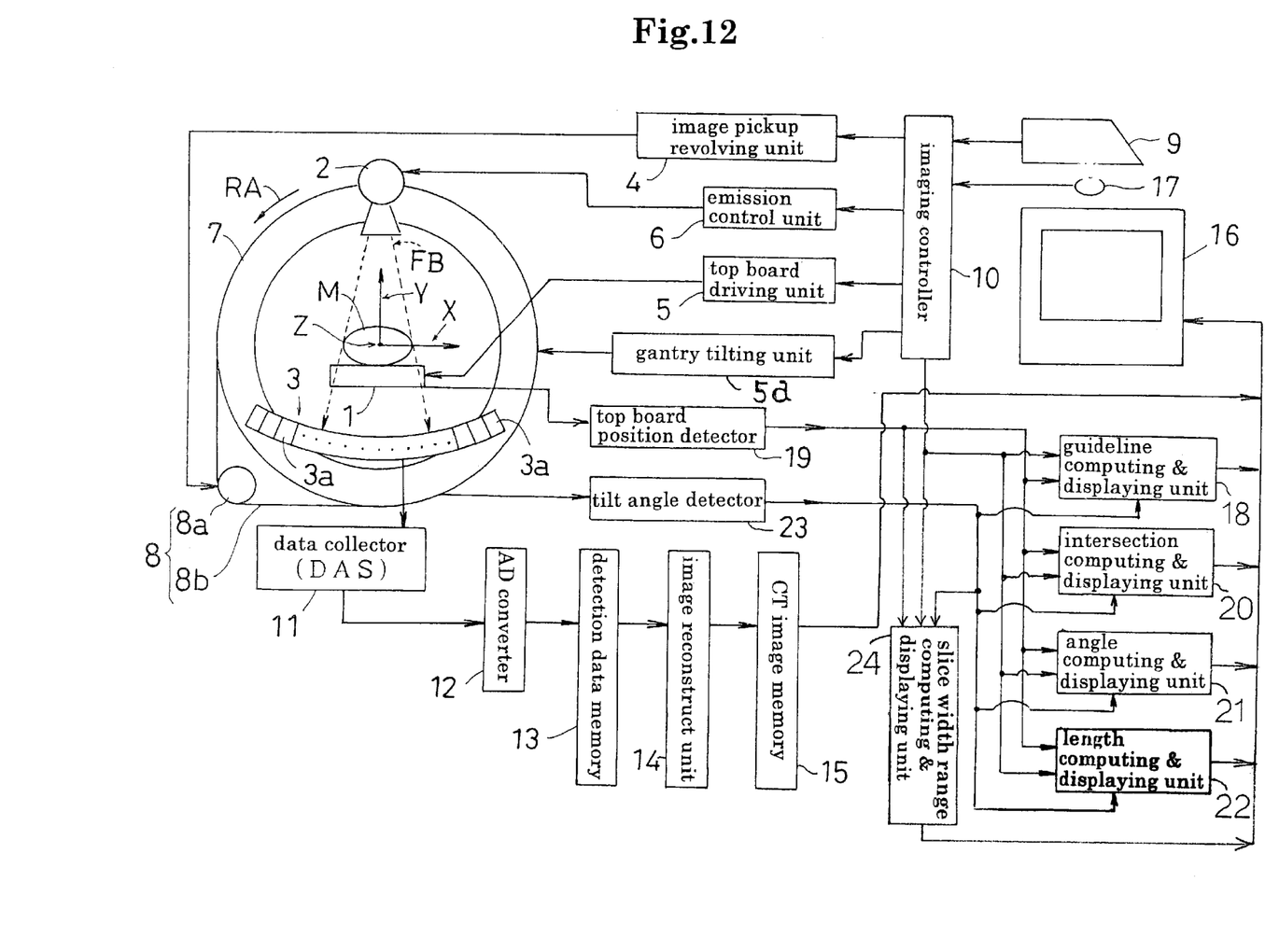
FIG. 12 is a block diagram of an entire X-ray CT apparatus in a second embodiment.

A radiographic apparatus in a second embodiment of this invention will be described next with reference to the drawings. FIG. 12 is a block diagram of an entire X-ray CT apparatus in the second embodiment of this invention. As seen from FIG. 12, the apparatus in the second embodiment additionally includes a slice width range computing and displaying unit 24. Otherwise, this apparatus has the same construction and effects as the first embodiment. To avoid repetition, the common features will be omitted from the following description and only different aspects will be described hereinafter.

Figure 13:
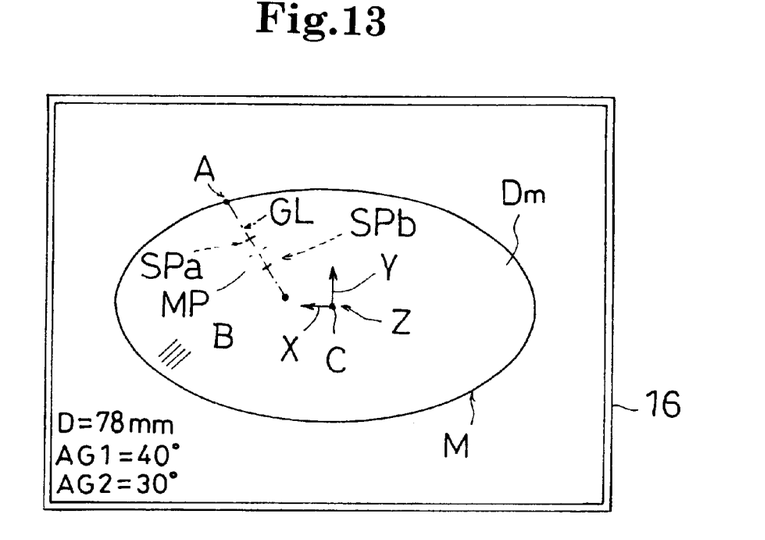
FIG. 13 is a front view of a display screen showing a guideline in the second embodiment.

In the apparatus in this embodiment, as shown in FIG. 13, the slice width range computing and displaying unit 24, in response to movement of the top board 1, successively computes a slice width range of the guideline GL corresponding to a slice thickness of each CT image on which the guideline GL is superposed. The slice width range computing and displaying unit 24 displays, as superposed on each CT image, range marks SPa and SPb indicative of the slice width range of guideline GL computed.

Figure 14:
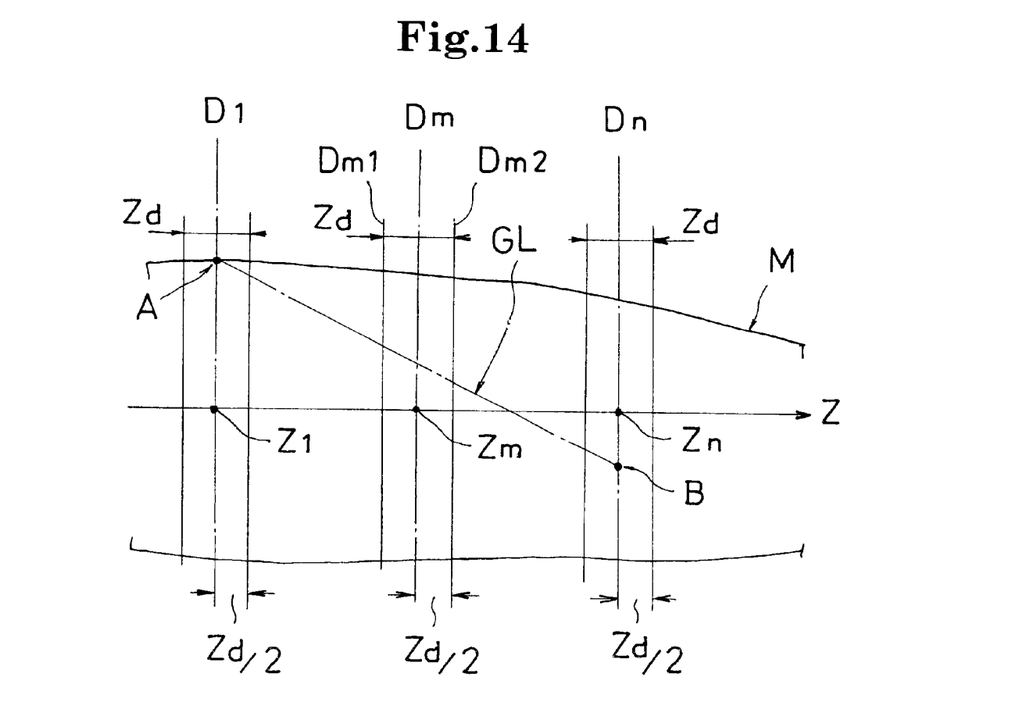
FIG. 14 is a schematic view showing a slice thickness to be imaged of a patient.

Strictly, with the X-ray CT apparatus, as shown in FIG. 14, the CT image of each slice plane D1, . . . Dm or Dn at Z coordinate Z1 . . . Zm or Zn includes, combined and, so to speak, compressed thereinto (along Z-axis) in the position of Z coordinate Z1 . . . Zm or Zn, data within a slice thickness Zd having an equal width $\Delta Z$ (Zd/2) in each opposite direction along Z-axis from Z coordinate Z1 . . . Zm or Zn. The biopsy needle, strictly speaking, is run along the guideline GL just by an amount equal to the slice thickness. To describe this aspect by taking the slice plane Dm for example, the intersection mark MP shown in FIG. 13 corresponds to an intersection of guideline GL and slice plane Dm in FIG. 14. On the other hand, the range marks SPa and SPb shown in FIG. 13 correspond to points formed by projecting, on the slice plane Dm, intersections of guideline GL and two opposed planes Dm1 and Dm2 spaced apart across the slice plane Dm by a distance corresponding to the slice thickness. Thus, strictly speaking, the intersection mark MP is at the midpoint between the two range marks SPa and SPb.

Specifically, the slice width range computing and displaying unit 24 is constructed to compute positions of range marks SPa and SPb indicative of a slice width range of guideline GL from a dimension of slice thickness Zd (e.g. approximately 10 mm) inputted from the console 9, and coordinates of needle entry point A and tissue collection point B inputted from the mouse 17. For the CT image of slice plane Dm, for example, the slice width range computing and displaying unit 24 computes an intersection of a straight line linking the two points A and B and an XY plane (i.e. plane Dm1) perpendicular to Z-axis in the position of Z coordinate Zm−Zd/2, and an intersection of the same straight line and an XY plane (i.e. plane Dm2) perpendicular to Z-axis in the position of Z coordinate Zm+Zd/2. The slice width range computing and displaying unit 24 then displays the points of projection of the two intersections on the slice plane, on the display monitor 16 as range marks SPa and SPb. For the CT images of the other slice planes, the same computation is performed, with only Z coordinate Zm changed to other coordinates.

Instead of the above construction, the slice width range computing and displaying unit may be constructed to compute angles of inclination of guideline GL with respect to X-, Y- and Z-axes, and determine, as positions of range marks SPa and SPb, points at distances corresponding to half (=Zd/2) the slice thickness Zd in opposite directions along the guideline GL from the intersection MP and corrected according to the angles of inclination of guideline GL.

Once the slice width range computing and displaying unit 24 displays the range marks SPa and SPb as superposed on each CT image, these marks serve as a reference for properly guiding the point Ka of biopsy needle K throughout the slice thickness.

Figure 15:
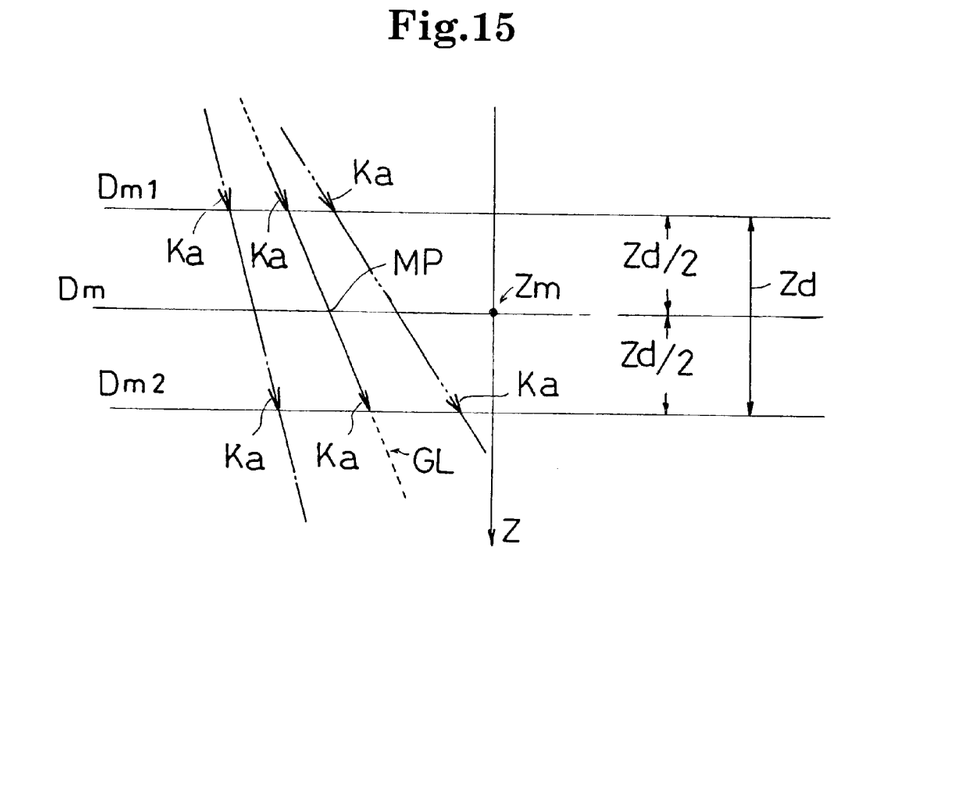
FIG. 15 is a schematic view showing running conditions of a biopsy needle in the second embodiment.
Figure 16A:
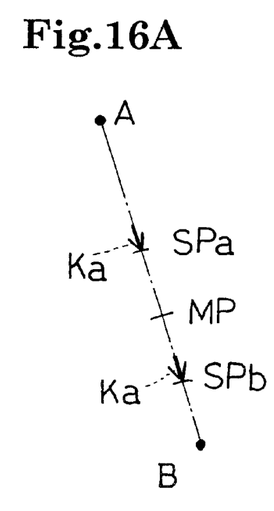
FIGS. 16A through 16C are schematic views showing movement of the needle point on the screen as the biopsy needle is run in the second embodiment.

When the biopsy needle K runs in alignment with the guideline GL throughout the slice thickness as shown in a solid line in FIG. 15, the needle point Ka emerges precisely in the position of range mark SPa and reaches the range mark SPb on the screen of display monitor 16 as shown in FIG. 16A. Therefore, the operator has only to run the biopsy needle K to move the point Ka from the starting end to the finishing end of the slice width range of guideline GL.

When the biopsy needle K deviates from the guideline GL, the needle point Ka usually deviates from the guideline GL on the screen of display monitor 16 also. However, depending on the way the biopsy needle K deviates from the guideline GL, the needle K could appear as if coinciding with the guideline GL to form a single line therewith. That is, the guideline GL, which is essentially a three-dimensional image, is displayed as superposed on the CT image, in a form projected to the slice plane as a two-dimensional image. When the biopsy needle K deviates on a plane including the three-dimensional guideline GL and extending perpendicular to the slice plane, the point Ka of biopsy needle K and the guideline GL appear to coincide on the CT image. However, where, as in the X-ray CT apparatus in this embodiment, the range marks SPa and SPb are displayed, the operator will understand that the needle point Ka appears to coincides with the guideline GL but in reality deviates therefrom.

Figure 16B:
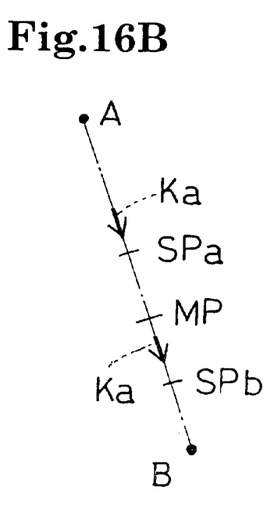

That is, when the biopsy needle K deviates from the guideline GL leftward in FIG. 15 as shown in a one-dot chain line and coincides with the guideline GL only apparently, the needle point Ka emerges upstream of the range mark SPa and stops short of the range mark SPb on the screen of display monitor 16 as shown in FIG. 16B. Thus, the operator can recognize that the biopsy needle K fails to follow the guideline GL correctly.

Figure 16C:
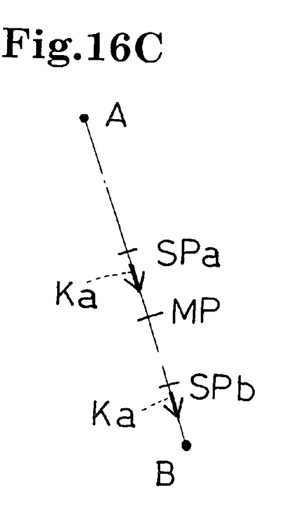

When the biopsy needle K deviates from the guideline GL rightward in FIG. 15 as shown in a two-dot chain line and coincides with the guideline GL only apparently, the needle point Ka emerges downstream of the range mark SPa and reaches beyond the range mark SPb on the screen of display monitor 16 as shown in FIG. 16C. Thus, the operator can recognize that the biopsy needle K fails to follow the guideline GL correctly.

Of course, the X-ray CT apparatus in this embodiment also not always picks up images from slice planes perpendicular to the body axis of patient M, but may pick up images from slice planes inclined relative to the body axis of patient M with the gantry C tilted at angle TA by the gantry tilting unit 5a as in the first embodiment. In this case, the tilt angle TA of gantry G must be taken into account when computing the range marks SPa and SPb. The apparatus in this embodiment includes a tilt angle detector 23 for detecting the tilt angle TA of gantry G, which transmits the tilt angle TA to the slice width range computing and displaying unit 24. Based on the tilt angle TA, the slice width range computing and displaying unit 24 replaces the coordinates with the device coordinates.

As described above, the apparatus in this embodiment displays the range marks SPa and SPb indicative of a slice width range of guideline GL existing within the slice thickness Zd of each CT image on which the guideline GL is superposed. These range marks SPa and SPb serve as a reference for guiding the point Ka of biopsy needle K throughout the slice thickness. Thus, the operator may run the biopsy needle K into the patient M accurately and quickly.

This invention is not limited to the embodiments described hereinbefore, but may be implemented with the following modifications:

(1) The embodiments have been described in relation to the X-ray CT apparatus. An MRI apparatus (magnetic resonance imaging apparatus) may be cited as a modification.

(2) The foregoing embodiments may be modified to include a laser light emitting device for emitting a laser beam to the patient M which indicates a direction corresponding to the angles AG1 and AG2 computed by the angle computing and displaying unit 21. By setting the longitudinal direction of biopsy needle K to the laser beam, the biopsy needle K may be run correctly in the direction indicated by the guideline GL.

(3) In the foregoing embodiments, the apparatus is operable to designate a set of a needle entry point and a tissue collection point and to compute and display one guideline. This invention is applicable to a construction for designating plural sets of needle entry points and tissue collection points, and computing and displaying a plurality of guidelines, all at a time.

(4) In the foregoing embodiments, the top board is movable to provide varied positions of CT images (slice planes). Instead, the top board may be fixed, with the image pickup adapted movable along the body axis of the patient to provide varied positions of CT images.

(5) In the second embodiment, the range marks SPa and SPb and the intersection MP are displayed as superposed on each CT image. The intersection MP, which is at the midpoint between the range marks SPa and SPb, may be located visually with some certainty even if not displayed, as long as the range marks SPa and SPb are displayed. Thus, an X-ray CT apparatus constructed to display only the range marks SPa and SPb as superposed on CT images may be cited as a modification.

(6) Though rare, the gantry may be tilted or the top board moved vertically in the course of running a biopsy needle into a patient while observing CT images. In this case, the guideline must be corrected for display. For example, a guideline previously derived is erased for safety's sake, and the operator is urged to re-set a needle entry point and a tissue collection point to determine and display a new guideline. Alternatively, the coordinates of the needle entry point and tissue collection point set previously may be corrected with a new tilt angle or top board height, to display a guideline, intersection marks and range marks based on corrected coordinates of the needle entry point and tissue collection point.

The present invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for shifting slice planes imaged of a patient and displaying sectional images of the slice planes in real time on a display monitor in response to running of a thrust needle into the patient, in order to assist in running the thrust needle from a body surface of the patient to a target point in the patient, said apparatus comprising:

> screen input means for designating and inputting a needle entry point on the body surface of the patient and said target point in the patient, on a screen of a display monitor displaying the sectional images; and
>
> guideline computing and displaying means for computing a line segment linking said needle entry point and said target point, and displaying said line segment as a guideline superposed on said sectional images of the slice planes for guiding said thrust needle.

2. A radiographic apparatus as defined in claim 1, further comprising intersection computing and displaying means for successively computing intersections of said slice planes and said guideline in response to shifting of said slice planes, and displaying intersection marks indicative of said intersections as superposed on said sectional images.

3. A radiographic apparatus as defined in claim 1, further comprising slice width range computing and displaying means for successively computing slice width ranges each extending between opposite ends of a portion of said guideline present within a slice thickness across each of said slice planes in response to shifting of said slice planes, and displaying said slice width ranges of said guideline as superposed on said sectional images.

4. A radiographic apparatus as defined in claim 1, further comprising angle computing and displaying means for computing angles between said guideline and predetermined reference axes, and displaying said angles simultaneously with said sectional images on said display monitor.

5. A radiographic apparatus as defined in claim 1, further comprising laser light emitting means for computing angles between said guideline and predetermined reference axes, and emitting to the patient a laser beam indicative of a direction corresponding to said angles to indicate a direction in which to run said thrust needle.

6. A radiographic apparatus as defined in claim 1, further comprising length computing and displaying means for computing a length of said guideline, and displaying said length simultaneously with said sectional images on said display monitor.

7. A radiographic apparatus as defined in claim 1, wherein said screen input means is capable of designating and inputting a plurality of needle entry points and a plurality of target points, said guideline computing and displaying means being operable, when said screen input means designates and inputs at least a plurality of needle entry points or a plurality of target points, to display, as superposed on said sectional images, a plurality of guidelines corresponding to said needle entry points and said target points.

8. A radiographic apparatus as defined in claim 1, wherein said radiographic apparatus is an X-ray CT apparatus.

9. A radiographic apparatus as defined in claim 1, wherein said radiographic apparatus is a magnetic resonance imaging apparatus.

10. A radiographic apparatus for shifting slice planes imaged of a patient and displaying sectional images of the slice planes in real time on a display monitor in response to running of a thrust needle into the patient, in order to assist in running the thrust needle from a body surface of the patient to an actual target point in the patient, said apparatus comprising:

> screen input means for designating and inputting a representative needle entry point located on a first selected slice plane displayed on a screen of the display monitor, the representative needle entry point being representative of an actual needle entry point on the body surface of the patient and a representative target point located on a second selected slice plane displayed on the screen of the display monitor, the first selected slice plane being different from the second selected slice plane, the representative target point being representative of the actual target point; and
>
> guideline computing and displaying means for computing a line segment linking said representative needle entry point and said representative target point, and displaying said line segment on the screen as a guideline superposed on said sectional images of the slice planes including the first and second selected slice planes for guiding said thrust needle.

11. A method for establishing a line segment as a guideline superposed on sectional images of slice planes displayed on a screen of a display monitor of a computer for running a thrust needle into a patient, the method comprising the steps of:

> displaying on the screen of the display monitor a first selected slice plane desirable for an actual needle entry point on a body surface of the patient;
>
> inputting a representative needle entry point at a selected location on an outer periphery of the first selected slice plane, the representative needle entry point corresponding with and being representative of the actual needle entry point;
>
> displaying on the screen of the display monitor a second selected slice plane desirable for an actual target point inside the patient, the second selected slice plane being different from the first selected slice plane;
>
> inputting a representative target point at a selected target point location inside the second selected slice plane, the representative target point corresponding with and being representative of the actual target point;
>
> establishing first coordinates of the representative needle entry point and second coordinates of the representative target point;
>
> computing the line segment based upon the first and second coordinates; and
>
> setting the line segment to be displayed as a guideline projected and superposed on said sectional images of the slice planes.

\* \* \* \* \*